United States Patent
Audebert et al.

(10) Patent No.: US 11,471,293 B2
(45) Date of Patent: Oct. 18, 2022

(54) GLENOIDAL IMPLANT FOR SHOULDER PROSTHESIS

(71) Applicant: SHOULDER FRIENDS INSTITUTE, Paris (FR)

(72) Inventors: Stephane Audebert, Blecourt (FR); Johannes Barth, Meylan (FR); Christophe Charousset, Paris (FR); Jerome Garret, Limonest (FR); David Gallinet, Geneuille (FR); Arnaud Godeneche, Saint Cyr au Mont d'Or (FR); Jacques Guery, Nevers (FR); Thierry Joudet, Libourne (FR); Yves Lefebvre, Strasbourg (FR)

(73) Assignee: SHOULDER FRIENDS INSTITUTE, Paris (FR)

( * ) Notice: Subject to any disclaimer, the term of this patent is extended or adjusted under 35 U.S.C. 154(b) by 0 days.

(21) Appl. No.: 16/885,663

(22) Filed: May 28, 2020

(65) Prior Publication Data
US 2020/0289281 A1 Sep. 17, 2020

Related U.S. Application Data

(63) Continuation of application No. PCT/FR2018/052997, filed on Nov. 27, 2018.

(30) Foreign Application Priority Data

Nov. 28, 2017 (FR) ...................................... 17/61298

(51) Int. Cl.
*A61F 2/40* (2006.01)
*A61B 17/17* (2006.01)
(Continued)

(52) U.S. Cl.
CPC .......... *A61F 2/4081* (2013.01); *A61F 2/4014* (2013.01); *A61B 17/1637* (2013.01);
(Continued)

(58) Field of Classification Search
CPC ..................... A61F 2/4081; A61F 2/40; A61F 2002/30116; A61F 2002/3012;
(Continued)

(56) References Cited

U.S. PATENT DOCUMENTS 6,364,910 B1 * 4/2002 Shultz ................ A61B 17/1659
606/86 R
8,690,951 B2 * 4/2014 Baum ................... A61F 2/4081
623/18.11
(Continued)

FOREIGN PATENT DOCUMENTS

EP 1762201 3/2007
FR 2937245 4/2010
(Continued)

OTHER PUBLICATIONS

International Search Report for International Application PCT/FR2018/052997, dated Apr. 10, 2019.

*Primary Examiner* — Brian A Dukert
(74) *Attorney, Agent, or Firm* — Burris Law, PLLC

(57) ABSTRACT

A glenoidal implant for a shoulder prosthesis includes an articular body having two opposite faces which are an articulation face suitable for cooperating with an articulation head of a humeral implant, and an anchoring face from which at least one anchoring stud protrudes for an anchoring in the glenoid cavity including a main anchoring stud at least partially covered with a porous or rough surface coating promoting an osseointegration. The main anchoring stud is provided internally with a central hole extending along a
(Continued)

central axis of symmetry of the main anchoring stud and provided to allow guiding a trephine.

11 Claims, 4 Drawing Sheets

(51) Int. Cl.
    *A61B 17/16*     (2006.01)
    *A61F 2/30*     (2006.01)

(52) U.S. Cl.
    CPC . *A61B 17/1778* (2016.11); *A61F 2002/30011* (2013.01); *A61F 2002/3093* (2013.01); *A61F 2002/30224* (2013.01); *A61F 2002/30322* (2013.01); *A61F 2002/30784* (2013.01); *A61F 2002/30884* (2013.01); *A61F 2002/30892* (2013.01); *A61F 2310/00407* (2013.01)

(58) Field of Classification Search
    CPC .. A61F 2002/30784; A61F 2002/30878; A61F 2002/30891; A61F 2002/30892
    See application file for complete search history.

(56) References Cited

U.S. PATENT DOCUMENTS

| | | | |
|---|---|---|---|
| 8,690,952 B2* | 4/2014 | Dallmann | A61F 2/4081 623/19.13 |
| 2007/0055380 A1* | 3/2007 | Berelsman | A61F 2/4081 623/19.11 |

FOREIGN PATENT DOCUMENTS

| | | |
|---|---|---|
| FR | 2971416 | 8/2012 |
| WO | 2016110758 | 7/2016 |
| WO | 2016164385 | 10/2016 |
| WO | 2017007565 | 1/2017 |

* cited by examiner

GLENOIDAL IMPLANT FOR SHOULDER PROSTHESIS

CROSS-REFERENCE TO RELATED APPLICATIONS

This application is a continuation of International Application No. PCT/FR2018/052997, filed on Nov. 27, 2018, which claims priority to and the benefit of FR 17/61298, filed on Nov. 28, 2017. The disclosures of the above applications are incorporated herein by reference.

FIELD

The present disclosure relates to a glenoidal implant for a shoulder prosthesis.

BACKGROUND

The statements in this section merely provide background information related to the present disclosure and may not constitute prior art.

A glenoidal implant conventionally comprises an articular body having two opposite faces which are an articulation face suitable for cooperating with an articulation head of a humeral implant, and an anchoring face from which at least one anchoring stud protrudes for an anchoring in the glenoid cavity of the scapula.

For the anchoring of a glenoidal implant in the glenoid cavity, it is conceivable to use a cemented anchoring in the bone, generally in the presence of bone structures which are less stable and of lower quality than necessary as for example due to an osteoporosis, or to a cementless anchoring.

For a cementless anchoring, it is known to use threaded anchoring studs and/or anchoring studs which are at least partially covered with a porous or rough surface coating promoting an osseointegration, as known for example from the document FR 2 971 416. It should be noted that a cement can be used in addition to such anchoring studs.

The state of the art can also be illustrated by the teaching of the document WO 2016/164385 which describes a glenoidal implant for a shoulder prosthesis, comprising an articular body which is composed of a front base (base plate) and a back plate (liner) which are fixedly assembled. Furthermore, this articular body has two opposite faces which are an articulation face on the back plate suitable for cooperating with an articulation head of a humeral implant, and an anchoring face on the front base from which a main anchoring stud, at least partially covered with a porous or rough surface coating, protrudes. This main anchoring stud is fastened to the front base and is provided internally with a central hole which internally receives a centering stud (centering feature) integrated into the back plate.

The document WO 2016/110758 discloses, in turn, a glenoidal implant for a shoulder prosthesis, comprising an articular body which is composed of a first portion and of a second portion which are fixedly assembled. This articular body has two opposite faces which are an articulation face on the second portion, and an anchoring face on the first portion from which a main anchoring stud, at least partially covered with a porous or rough surface coating, protrudes. Moreover, and as shown in FIGS. 4 and 5 of WO 2016/110758, this main anchoring stud is integral with the first portion and it is provided internally with a central hole which is a through hole (otherwise it opens onto the free end of the main anchoring stud) and it is provided to receive a centering stud which is integral with the second portion. This centering stud receives, in turn, internally a screw accessible by the articulation face and which participates in the blocking of the centering stud inside the central hole in the main anchoring stud, and therefore in a locking between the first portion and the second portion.

An anchoring stud with a porous or rough surface coating has the advantage that, after implantation in the glenoid cavity, the pores are invaded by the growing bone cells to promote an osseointegration of this anchoring stud.

However, if a recovery or removal of the glenoidal implant is necessary, the osseointegration of such an anchoring stud forces the surgeon to remove, conventionally by means of a trephine (or hole saw), a large bone portion of the glenoid cavity to completely extract the anchoring stud, with the chance of impairing the anchoring of the future glenoidal implant which will replace the removed glenoidal implant. Indeed, the preservation of the bone capital is a success factor of the surgical recovery.

SUMMARY

This section provides a general summary of the disclosure and is not a comprehensive disclosure of its full scope or all of its features.

The present disclosure provides a glenoidal implant having an anchoring stud with a porous or rough surface coating, and which allows, during a recovery of the glenoidal implant, guiding the surgeon in the removal operation thereof so that he removes the minimum of bone in the glenoid cavity to extract the anchoring stud.

For this purpose, present disclosure provides a glenoidal implant for a shoulder prosthesis, comprising an articular body having two opposite faces which are an articulation face suitable for cooperating with an articulation head of a humeral implant, and an anchoring face from which at least one anchoring stud protrudes for an anchoring in the glenoid cavity including a main anchoring stud at least partially covered with a porous or rough surface coating promoting an osseointegration, in which the main anchoring stud is provided internally with a central hole extending along a central axis of symmetry of the main anchoring stud, and in which the main anchoring stud is fixedly mounted on the anchoring face of the articular body, and this main anchoring stud has two opposite ends which are a proximal end secured to the anchoring face and in which the central hole opens, and a blocked distal end, this glenoidal implant being remarkable in that the central hole extends over at least 80% of a length of the main anchoring stud measured between the proximal end and the distal end to allow guiding a trephine.

Thus, during an operation of recovery of the glenoidal implant, the surgeon might, after accessing the central hole of the main anchoring stud, engage a central guide of a trephine in this central hole (the central guide of the trephine defining the axis of symmetry of the circular cutout implemented by the trephine) and could thus guide the trephine to cut the bone in an adjusted manner around the main anchoring stud, thus limiting the dimension of the cutout orifice which will remain once the main anchoring stud is extracted.

Moreover, this central hole is deep enough (its depth being at least equal to 80% of the length of the main anchoring stud to be removed during a recovery operation) to precisely allow such a recovery, in an accurate, stable and complete manner, by means of the trephine engaged in this central hole.

Advantageously, the central hole is empty on at least 80% of its depth, and in one form, the central hole is empty over its entire depth.

Thus, this central hole is empty or almost empty to promote the insertion and the passage of the trephine without a stud hindering it.

According to one possibility, the central hole has an entrance on the proximal end of the main anchoring stud, and this entrance is blocked by the articular body.

Thus, this central hole does not open into the articulation face, which allows having no debris which would penetrate inside the central hole and which would then impair the guiding of the trephine. Moreover, during an operation of recovery of the glenoidal implant, the surgeon will be able to access the central hole of the main anchoring stud after having pierced the articular body.

In one particular form, the main anchoring stud is fixedly mounted on the anchoring face of the articular body, and this main anchoring stud has two opposite ends which are a proximal end secured to the anchoring face and in which the central hole opens, and a blocked distal end, said central hole being blind.

According to one feature, the main anchoring stud has a peripheral groove at the proximal end, and the main anchoring stud is fixedly mounted on the anchoring face of the articular body by overmolding the articular body in the peripheral groove.

According to another feature, the central hole has a conical or chamfered entrance on the proximal end of the main anchoring stud, in order to guide the insertion of the central guide of the trephine inside the central hole.

Advantageously, the anchoring face of the articular body has a plurality of recesses forming a macrostructure intended to promote a pressurization of a cement layer which would be inserted between the anchoring face and the bone.

According to one possibility of the present disclosure, a secondary anchoring stud protrudes from the anchoring face of the articular body.

According to another possibility of the present disclosure, this secondary anchoring stud is a conical stud being integral with the articular body.

In another particular form, the articular body has a plane of symmetry and has edges connecting the articulation face and the anchoring face and comprising:

a lower edge matching a main circle having a predefined main diameter and a main center placed on the plane of symmetry;

an upper edge matching a secondary circle having a predefined secondary diameter less than the main diameter and a secondary center placed on the plane of symmetry and offset relative to the main center; and two lateral edges joining the lower edge and the upper edge on either side of the plane of symmetry, wherein the central axis of symmetry of the main anchoring stud intersects the main center.

According to a variant, the articular body is a one-piece body.

The present disclosure also relates to a shoulder prosthesis comprising a glenoidal implant according to the present disclosure described above, and further comprising a humeral implant provided for an anchoring on a humerus and comprising an articulation head shaped to be joint on the articulation face of the articular body of the glenoidal implant.

Further areas of applicability will become apparent from the description provided herein. It should be understood that the description and specific examples are intended for purposes of illustration only and are not intended to limit the scope of the present disclosure.

DRAWINGS

In order that the disclosure may be well understood, there will now be described various forms thereof, given by way of example, reference being made to the accompanying drawings, in which:

FIG. 6 is a schematic side view of the glenoidal implant of FIGS. 1 to 3;

Figure 1:
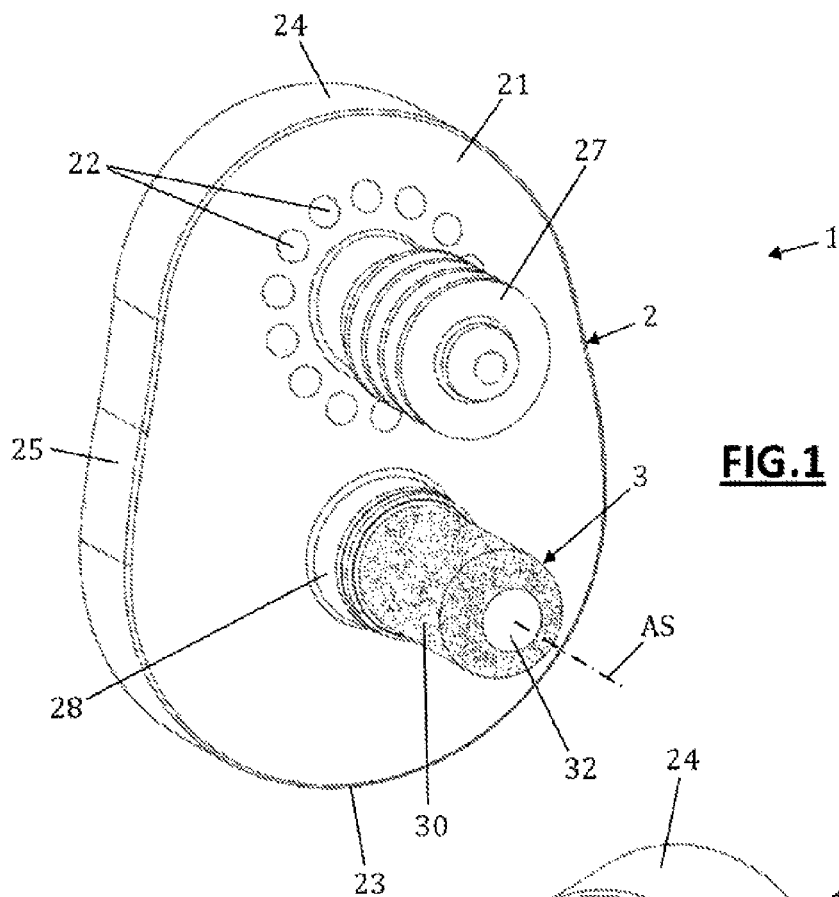
FIGS. 1 to 3 are schematic perspective views of a glenoidal implant from three distinct viewing angles according to the present disclosure.

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

With reference to FIGS. 1 to 6, a glenoidal implant 1, according to one form of the present disclosure, comprises an articular body 2 having two opposite faces 20, 21 which are an articulation face 20 suitable for cooperating with an articulation head of a humeral implant, and an anchoring face 21 provided for an anchoring in the glenoid cavity of the scapula.

The articular body 2 is a one-piece body made of a plastic or polymeric material, such as, for example, polyethylene, and in particular high density or ultra high molecular weight polyethylene (UHMWPE) or cross-linked polyethylene (XPE).

Figure 2:
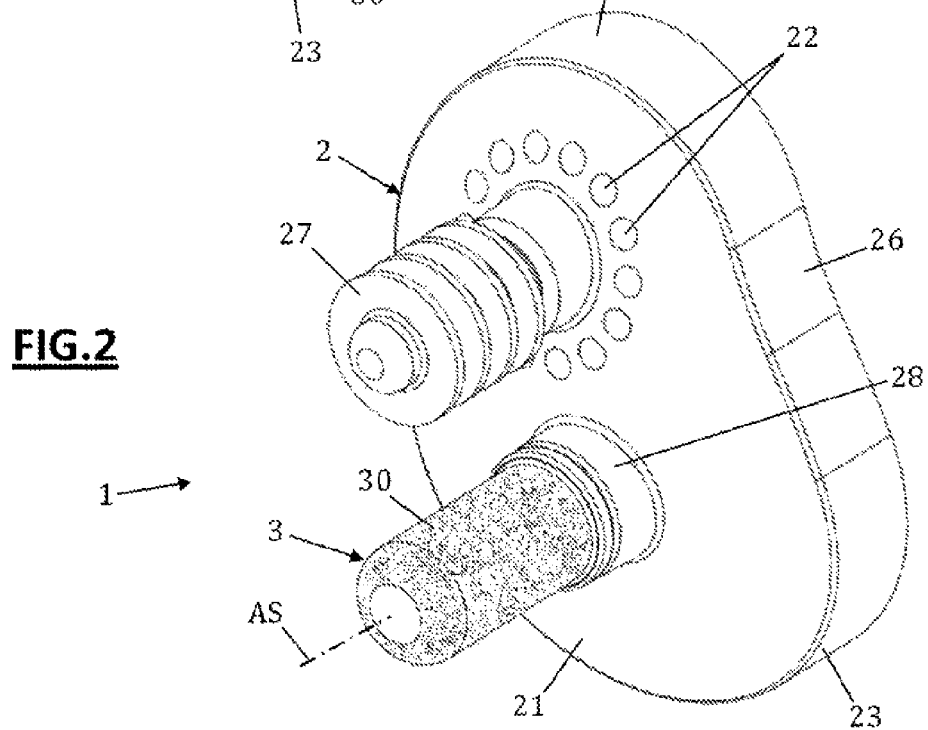
Figure 3:
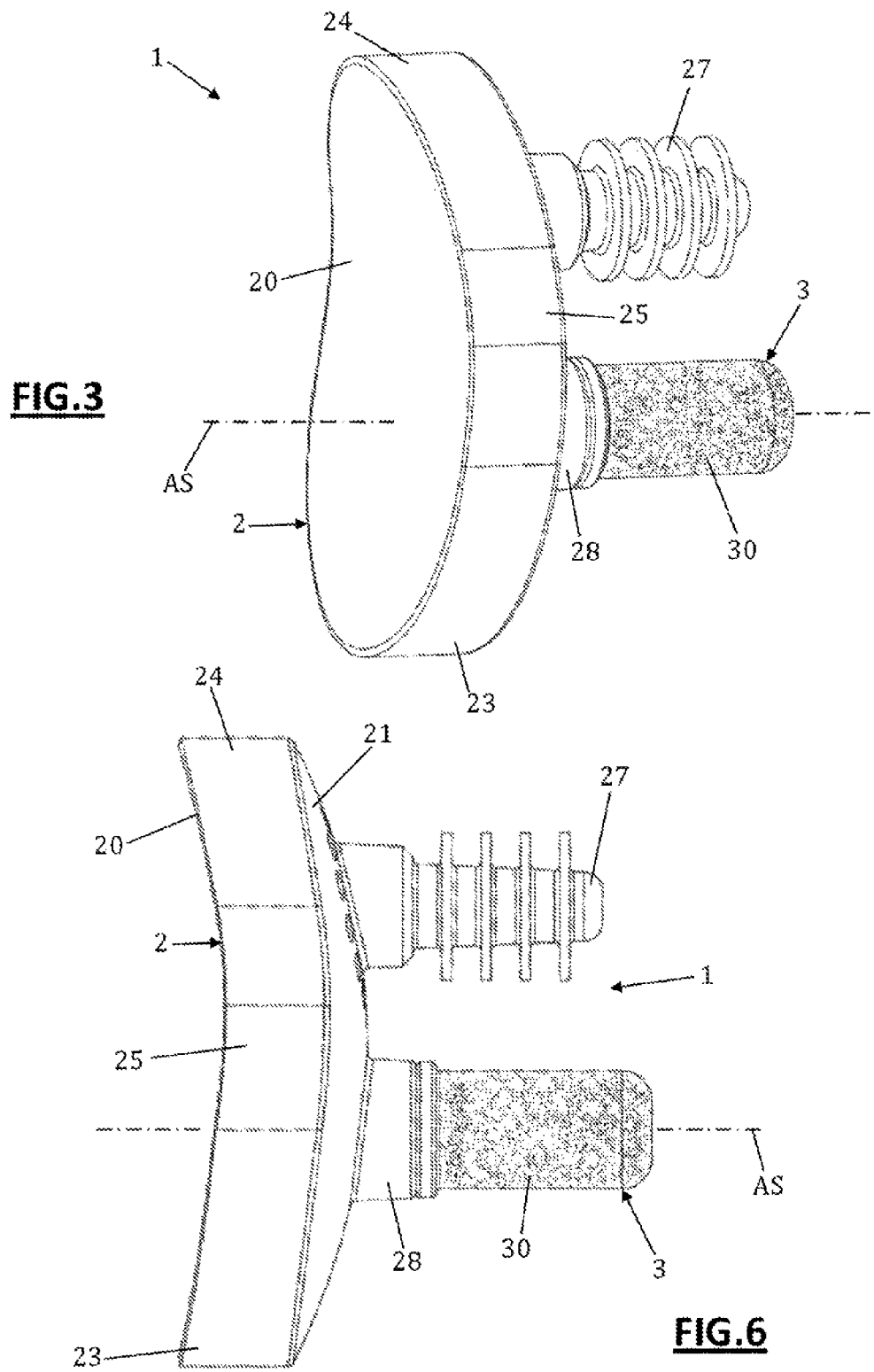
Figure 4:
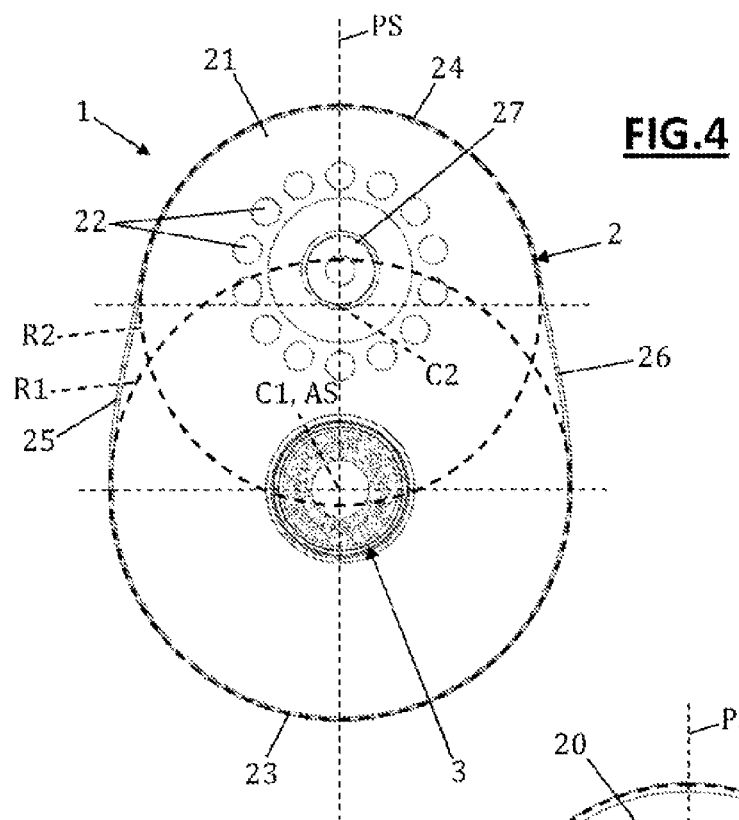
FIG. 4 is a schematic back view of the glenoidal implant of FIGS. 1 to 3.

As shown in FIGS. 1, 2 and 4, the anchoring face 21 of the articular body has a plurality of recesses 22 forming a macrostructure intended to promote a compression of a cement layer which would be inserted between the anchoring face 21 and the bone; these recesses 22 might be in the form of drill point recesses by way of non-limiting example.

Figure 5:
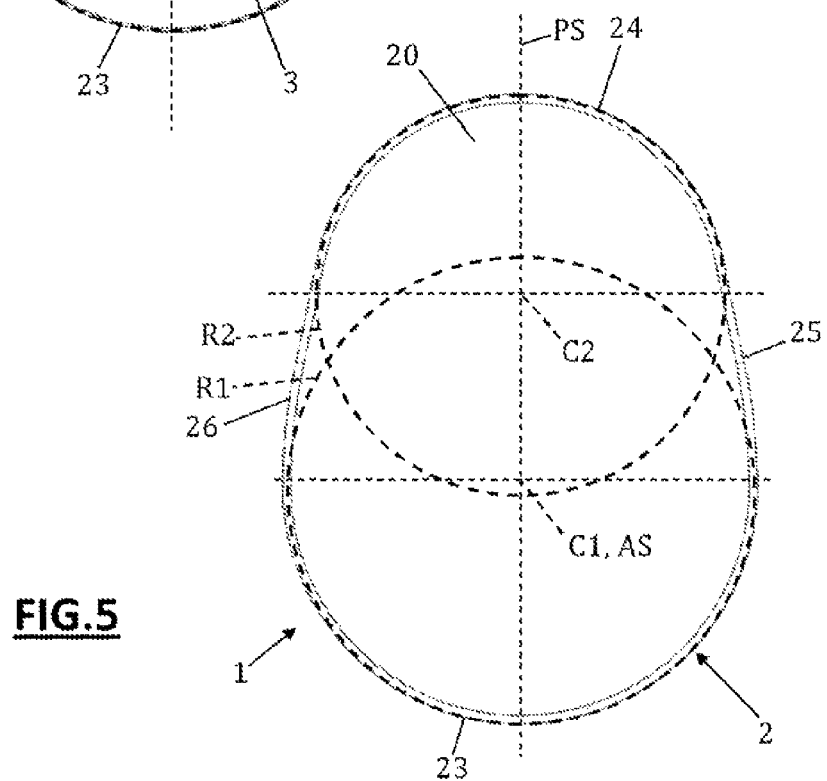
FIG. 5 is a schematic front view of the glenoidal implant of FIGS. 1 to 3.

As shown in FIGS. 4 and 5, the articular body 2 has a plane of symmetry PS and has edges 23, 24, 25, 26 connecting the articulation face 20 and the anchoring face 21, these edges 23, 24, 25, 26 forming the peripheral perimeter of the articular body 2 and defining the thickness of the articular body 2.

These edges 23, 24, 25, 26 comprise:

a lower edge 23 matching a main circle R1 having a predefined main diameter D1 and a main center C1 placed on the plane of symmetry PS;

an upper edge 24 matching a secondary circle R2 having a predefined secondary diameter D2 less than the main diameter D1 and a secondary center C2 placed on the plane of symmetry PS and offset relative to the main center C1; and two lateral edges 25, 26 joining the lower edge 23 and the upper edge 24 on either side of the plane of symmetry PS.

Furthermore, the articular body 2 comprises a secondary anchoring stud 27 which protrudes from the anchoring face 21 and which is integral with the articular body 2. In the example illustrated in the figures, the secondary anchoring stud 27 is a conical stud provided with cylindrical fins spaced from each other. In a variant which is not illustrated, the secondary anchoring stud 27 can be a conical and smooth stud.

The secondary anchoring stud 27, located in the plane of symmetry PS, is surrounded by the secondary circle R2 and is more specifically placed between the secondary center C2 and the top of the upper edge 24 which corresponds to the point of the upper edge 24 located in the plane of symmetry PS.

In the example illustrated in the figures, the aforementioned recesses 22 are disposed on the periphery of the secondary anchoring stud 27.

The glenoidal implant 1 further comprises a main anchoring stud 3 which protrudes from the anchoring face 21 and which is fixedly mounted on the anchoring face 21, wherein the main anchoring stud 3 is at least partially covered with a porous or rough surface coating 30 promoting an osseointegration.

The main anchoring stud 3 is a stud of revolution centered on a central axis of symmetry AS which intersects the main center C1 defined above.

The main anchoring stud 3 has two opposite ends which are a proximal end 31 secured to the anchoring face 21 and a free distal end 32.

Figure 7:
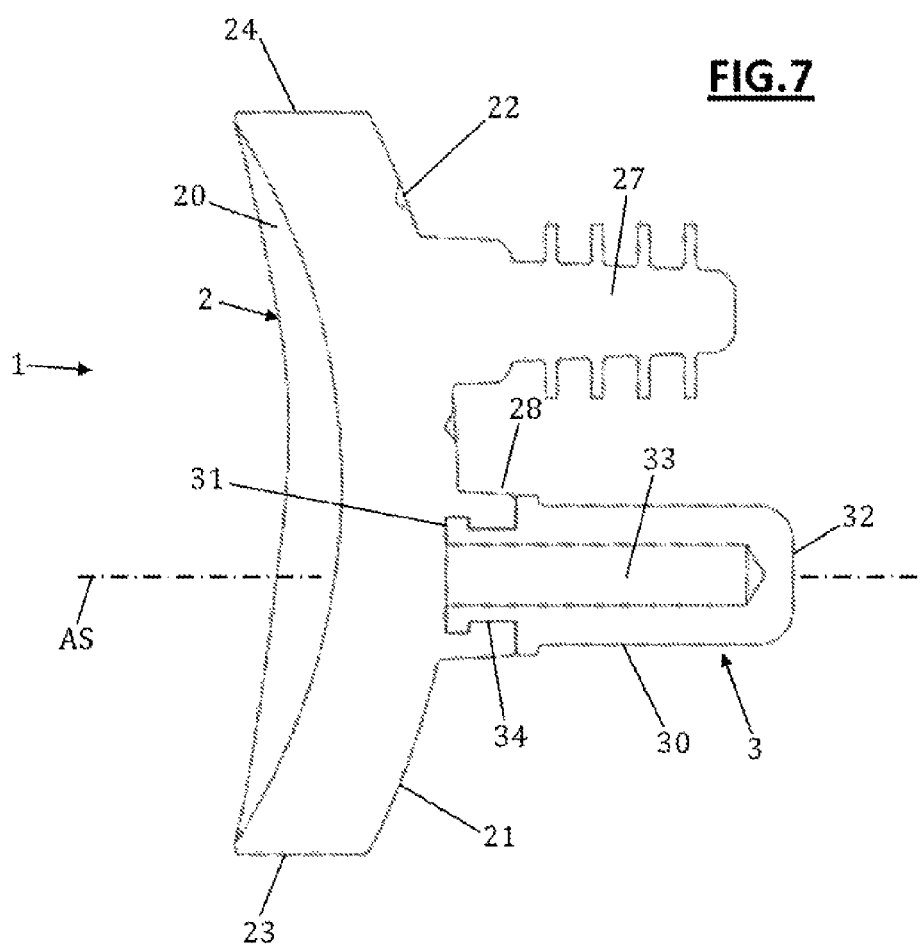
FIG. 7 is a cross-sectional view of the glenoidal implant of FIGS. 1 to 3 along a section plane corresponding to the plane of symmetry.
Figure 8:
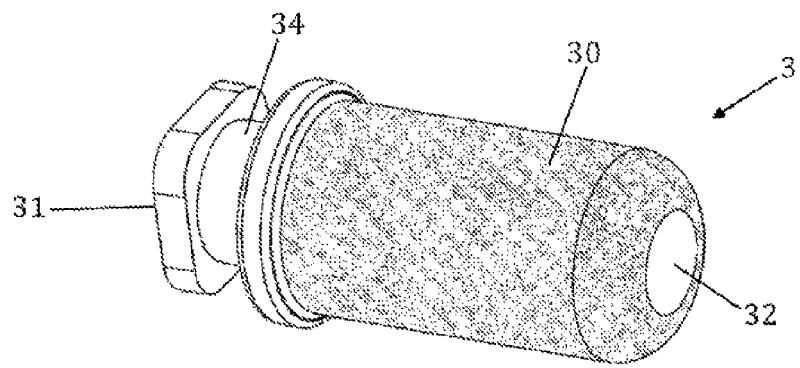
FIG. 8 is a schematic perspective view of the main anchoring stud alone.

As illustrated in FIG. 7, the main anchoring stud 3 is internally disposed with a blind central hole 33 which opens into the proximal end 31, such that the distal end 32 is blocked. The central hole 33 provided to allow guiding a trephine, as previously explained.

The central hole 33 extends over at least 80% of a length of the main anchoring stud 3 measured between the proximal end 31 and the distal end 32. The central hole 33 therefore has a depth measured between the proximal end 31 and the bottom of the central hole 33, and the depth is greater than or equal to 0.8 times the length of the main anchoring stud 3.

Moreover, and as shown in FIG. 7, the central hole 33 is empty over at least 80% of its depth and even over its entire depth. In other words, no element external to the central hole 33 is inserted inside the central hole 33 which is unoccupied.

The central hole 33 has an entrance on the proximal end 31 of the main anchoring stud 3, wherein this entrance can be conical or chamfered to facilitate later insertion of the trephine, and moreover this entrance is blocked by the articular body 2 by being embedded inside the articular body 2. Thus, the central hole 33 does not open into the articulation face 20, in other words the central hole 33 is not accessible from the side of the articulation face 20, and it is therefore desirable to pierce the articular body to access the entrance of the central hole 33 for the trephine.

The main anchoring stud 3 has a peripheral groove 34 at the proximal end 31, and the main anchoring stud 3 is fixedly mounted on the anchoring face 21 by overmolding the articular body 2 in the peripheral groove 34. In other words, the articular body 2 has, on the anchoring face 21 thereof, a boss 28 which overmolds the peripheral groove 34 of the main anchoring stud 3; the boss 28 being an integral part of the articular body 2.

The porous or rough surface coating 30 extends along the entire periphery of the main anchoring stud 3, between the peripheral groove 34 and the distal end 32.

The porous or rough surface coating 30 can for example comprise a layer of porous or rough titanium or of a porous or rough titanium alloy, and possibly further comprise a layer of calcium phosphate, such as calcium hydroxyapatite.

The glenoidal implant 1 can be used without cement with an anchoring in the glenoid cavity which then dependents on the effectiveness of the main anchoring stud 3 and the reintegration of the bone into the porous or rough surface coating 30 thereof.

The glenoidal implant 1 can also be partially cemented, by using a cement layer between the anchoring face 21 and the bone, without this cement layer projecting on the porous or rough surface coating 30. In the case of such a use with cement, the recesses 22 will allow a compression of the cement, which will improve its resistance.

It should be noted that the secondary anchoring stud 27 has the main function of providing a blocking in rotation of the articular body 2 on the glenoid cavity.

Of course, the example of implementation mentioned above is in no way limiting and other improvements and details can be made to the glenoidal implant according to the present disclosure, without departing from the scope of the present disclosure wherein other shapes or numbers of secondary anchoring studs can for example be made.

Unless otherwise expressly indicated herein, all numerical values indicating mechanical/thermal properties, compositional percentages, dimensions and/or tolerances, or other characteristics are to be understood as modified by the word "about" or "approximately" in describing the scope of the present disclosure. This modification is desired for various reasons including industrial practice, material, manufacturing, and assembly tolerances, and testing capability.

As used herein, the phrase at least one of A, B, and C should be construed to mean a logical (A OR B OR C), using a non-exclusive logical OR, and should not be construed to mean "at least one of A, at least one of B, and at least one of C."

The description of the disclosure is merely exemplary in nature and, thus, variations that do not depart from the substance of the disclosure are intended to be within the scope of the disclosure. Such variations are not to be regarded as a departure from the spirit and scope of the disclosure.

What is claimed is:

1. A glenoidal implant for a shoulder prosthesis, the glenoidal implant comprising:
    an articular body having two opposite faces including an articulation face and an anchoring face; and
    at least one anchoring stud protruding from the anchoring face and including a main anchoring stud at least partially covered with a porous or rough surface coating,
wherein the main anchoring stud includes a central hole extending along a central axis of symmetry of the main anchoring stud, the main anchoring stud is fixedly mounted on the anchoring face of the articular body such that the central hole is unoccupied, and the main anchoring stud has two opposite ends including a proximal end secured to the anchoring face and in which the central hole opens, and a blocked distal end, the central hole being blind and extending over at least 80% of a length of the main anchoring stud measured between the proximal end and the blocked distal end, and wherein the main anchoring stud is configured to receive a surgical tool.

2. The glenoidal implant according to claim 1, wherein at least 80% of a depth of the central hole is empty.

3. The glenoidal implant according to claim 2, wherein an entire depth of the central hole is empty.

4. The glenoidal implant according to claim 1, wherein the central hole has an entrance on the proximal end of the main anchoring stud, the entrance being blocked by the articular body.

5. The glenoidal implant according to claim 1, wherein the main anchoring stud has a peripheral groove at the proximal end, and the main anchoring stud is fixedly mounted on the anchoring face of the articular body by overmolding the articular body in the peripheral groove.

6. The glenoidal implant according to claim 1, wherein the anchoring face of the articular body has a plurality of recesses forming a macrostructure to promote pressurization of a cement layer inserted between the anchoring face and a bone.

7. The glenoidal implant according to claim 1, wherein a secondary anchoring stud protrudes from the anchoring face of the articular body.

8. The glenoidal implant according to claim 7, wherein the secondary anchoring stud is a conical stud being integral with the articular body.

9. The glenoidal implant according to claim 1, wherein the articular body has a plane of symmetry and edges connecting the articulation face and the anchoring face, the edges comprising:
 a lower edge matching a main circle having a main diameter and a main center placed on the plane of symmetry;
 an upper edge matching a secondary circle having a predefined secondary diameter less than the main diameter and a secondary center placed on the plane of symmetry and offset relative to the main center; and
 two lateral edges joining the lower edge and the upper edge on either side of the plane of symmetry,
wherein the central axis of symmetry of the main anchoring stud intersects the main center.

10. The glenoidal implant according to claim 1, wherein the articular body is a one-piece body.

11. A glenoidal implant for a shoulder prosthesis, the glenoidal implant comprising:
 an articular body having two opposite faces including an articulation face and an anchoring face; and
 at least one anchoring stud protruding from the anchoring face and including a main anchoring stud at least partially covered with a porous or rough surface coating,
wherein the main anchoring stud includes a central hole extending along a central axis of symmetry of the main anchoring stud, the main anchoring stud is fixedly mounted on the anchoring face of the articular body such that the central hole is unoccupied, and the main anchoring stud has two opposite ends including a proximal end secured to the anchoring face and in which the central hole opens, and a blocked distal end, the central hole being blind and extending substantially an entire length of the main anchoring stud measured between the proximal end and the blocked distal end, and
wherein the main anchoring stud is configured to receive a surgical tool.

* * * * *